United States Patent [19]

Goldstein

[11] Patent Number: 4,699,880
[45] Date of Patent: Oct. 13, 1987

[54] METHOD OF PRODUCING MONOCLONAL ANTI-IDIOTYPE ANTIBODY

[75] Inventor: Neil I. Goldstein, New Brunswick, N.J.

[73] Assignee: Immunomedics, Inc., Newark, N.J.

[21] Appl. No.: 654,273

[22] Filed: Sep. 25, 1984

[51] Int. Cl.[4] ...................... C12N 5/00; G01N 33/577
[52] U.S. Cl. ..................................... 435/172.2; 435/7; 435/240.27; 436/531; 436/548; 436/804; 530/387; 530/412; 935/93; 935/103; 935/110
[58] Field of Search ............... 436/518, 548, 808, 531, 436/804; 435/172.2, 240, 7, 241; 935/93, 103, 110; 530/387, 412

[56] References Cited

U.S. PATENT DOCUMENTS 4,238,195 12/1980 Boguslaski .......................... 435/7 X
4,513,088 4/1985 Levy ................................. 435/240 X
4,536,479 8/1985 Vander-Mallie .................... 436/537

OTHER PUBLICATIONS

"Contemporary Topics in Molecular Immunology", vol. 8, F. P. Inman et al., eds., Chapt. by J. Urbain entitled Idiotypic Regulation in Immune Networks, p. 119 only, Plenum Press, New York, 1981.
Suzan, M. et al., Molecular Immunology, 19(8), 1051–1062 (1982).

Primary Examiner—Sidney Marantz
Attorney, Agent, or Firm—Bernhard D. Saxe

[57] ABSTRACT

A method for determining the presence of an antigen in a liquid sample. The method includes incubating the sample with an antibody which specifically binds an epitope on the antigen in the presence of a given quantity of an anti-idiotype antibody which specifically binds an epitope on the hypervariable region of the antibody. Also, a method of producing a monoclonal anti-idiotype antibody by fusing lymphocytes from an animal in which a tumor capable of secreting idiotype antibodies has been grown, with myeloma cells.

6 Claims, No Drawings

METHOD OF PRODUCING MONOCLONAL ANTI-IDIOTYPE ANTIBODY

BACKGROUND OF THE INVENTION

The present invention relates to an immunoassay system which uses anti-idiotype antibodies in place of antigen and which is therefore antigen-independent. The invention also relates to a method for generating anti-idiotype antibodies.

The competitive immunoassay has classically been used to determine the presence of an antigen in a sample by measuring the inhibition of formation of a standard antigen-antibody complex, one of which is typically bound and the other of which is typically labeled, by free antigen in the sample. In addition, a typical quantitative immunoassay kit will include a standardized sample of pure antigen so that a reference solution can be run together with the sample to minimize sampling errors and to assure precision. In many cases, the antigen may be quite difficult to isolate and purify, and may also be of limited stability.

Antibodies which recognize the hypervariable or idiotype region of an antibody have been implicated in the regulation of the immune system. They are known as anti-idiotypes (a-Id). Thus, an antibody which specifically binds a particular antigen (a-Ag) will also specifically bind its complementary a-Id. It has been suggested that a complementary a-Ag/a-Id antibody pair could be used in a competitive immunoassay wherein antigen in the sample would compete with a-Id for labeled a-Ag, the extent of a-Id/a-Ag complex formation being inversely proportional to the antigen concentration in the sample. See, e.g., Potocnjak et al, *Science,* 215, 1637 (1982); and Mitchell et al, *Aust. J. Exp. Biol. Med. Sci.,* 61, 27 (1983). However, there has been no suggestion of using a-Id antibodies as a substitute for purified antigen for the reference component of a competitive immunoassay kit, which would permit accurate, quantitative immunoassays which are antigen-independent.

Typically, a-Ids are produced by challenging an animal with the a-Ag, in an antigenically active form, and recovering antiserum, or recovering lymphocytes and fusing them with myeloma cells to form hybridomas. There is no suggestion of using lymphocytes from an animal in which a hybridoma tumor is growing and secreting monoclonal a-Ags, as a source of a-Ids.

OBJECTS OF THE INVENTION

One object of the present invention is to provide a competitive immunoassay method which will be independent of the need for purified antigen in its routine application.

Another object of the invention is to provide a method of producing anti-idiotype antibodies which is simpler and more advantageous than conventional methods.

Upon further study of the specification and appended claims, further objects and advantages of this invention will become apparent to those skilled in the art.

SUMMARY OF THE INVENTION

These objects can be achieved by providing a method for determining the presence of an antigen (Ag) in a liquid sample, comprising the steps of:
  (a) incubating said sample with an antibody (a-Ag) which specifically binds an epitope on said antigen, in the presence of a given quantity of an anti-idiotype antibody (a-Id) which specifically binds an epitope on the hypervariable region of said a-Ag, at least one of said a-Ag and said a-Id being labeled, and measuring the extent of a-Ag.a-Id complex formation;
  (b) incubating a standard solution of unlabeled a-Id with said a-Ag and said quantity of a-Id, labeled as in step (a), and measuring a standard value for the extent of a-Ag.a-Id complex formation;
  whereby the presence of said antigen can be determined from the relative extents of a-Ag.a-Id complex formation in steps (a) and (b).

The invention further provides a method of producing a monoclonal anti-idiotype antibody, comprising the steps of:
  (a) fusing lymphocytes from an animal in which a hybridoma tumor capable of secreting idiotype antibodies has been grown, with myeloma cells; and
  (b) isolating and cloning resultant hybridoma cells secreting monoclonal antibodies which specifically bind an epitope on the hypervariable region of said idiotype antibodies.

DETAILED DISCUSSION

Competitive immunoassays, e.g., radioimmunoassay (RIA), enzyme-linked immunoadsorbant assay (ELISA) and the like are conventionally used to detect and quantitate the presence of antigen in a sample by determining the extent of inhibition of an antigen/antibody reaction. Typically, either the antigen or the antibody is bound to a solid support, while the other component of the pair is labeled in some fashion to render it detectable. Such labels often include, e.g., radioisotopes, enzymes, fluorescent markers and the like, all of which are well known in the art.

The label may be directly linked to the component or may be bound to it indirectly, e.g., by attaching the label to another molecule capable of recognizing a component of the antigen/antibody pair. For example, an antibody can be indirectly labeled by attaching an enzyme, fluorescent marker or radioisotope to an isotype-specific antibody which recognizes the non-variable region of the antigen-specific antibody. Alternatively, the label can be attached to an antibody which recognizes an available epitope of the antigen after it has been bound to the specific antibody. It will be appreciated that many other variants of this broad concept are possible and known to the art.

A number of advantages are realized by substituting an anti-idiotype antibody for the antigen in a competitive immunoassay. However, prior art suggestions for such substitution involved substituting labeled a-Id for labeled antigen in the primary competitive reaction of the assay. Unlabeled antigen was always used to test for inhibition. However, in a routine assay, it is disadvantageous to require purified antigen at any point. Antigens are often difficult to isolate and purify and are often of limited stability. The present invention provides the further advantage that reference measurements are made using unlabeled a-Id, making the entire routine determination antigen-independent.

It will be understood that characterization of the relative effectiveness of the antigen and the a-Id as inhibitors of the a-Ag/a-Id complex must be done initially, but the uniformity and stability of antibodies, especially monoclonal antibodies, obviates the need for continuous calibration and/or standardization of the a-Ids.

Several embodiments of the process of the invention are suitable, although the invention will not be limited to those specifically described herein, since alternative embodiments will be readily apparent to the ordinary skilled art worker. These illustrative embodiments will be described in detail hereinafter.

In a first preferred embodiment, an antibody which specifically binds an antigen which it is desired to determine, the antibody preferably being a monoclonal antibody with high specificity for the subject antigen, will be bound to a solid support for ease of separation. This is conventionally effected in a number of ways, e.g., treating a polyvinyl chloride test tube with an Ag, introducing a given quantity of radiolabeled a-Id, together with a measured volume of sample, and determining the degree of inhibition of binding of the labeled a-Id to the a-Ag coated test tube. A reference determination is made using a measured amount of unlabeled a-Id, whose capacity to inhibit the a-Ag/a-Id complex formation has previously been quantified and correlated with known amounts of antigen.

An alternative preferred embodiment involves binding the a-Id to the solid support and labeling the specific a-Ag. Again, the concentration of antigen in the sample will inhibit binding of the labeled component to the solid support and the extent of inhibition will be correlated with the standard curve using unlabeled a-Id and labeled a-Ag.

It will be understood that the term "antibody" as used herein includes all idiotypes, e.g., IgM, IgG, IgA, IgD and IgE, isotypes thereof, e.g., IgG1, IgG2 and the like, as well as fragments thereof, e.g., $F(ab')_2$, Fab, Fab' and the like. Either or both of the a-Ag and a-Id can be a whole antibody or an antibody fragment.

The method of the invention is especially useful in competitive immunoassays for tumor-associated antigens. Antibodies, particularly monoclonal antibodies, to antigens which are produced by or associated with various types of tumors and/or cancer-related pathologies, have been developed in recent years. A number of such antibodies, which are also useful for radioimmunodetection of cancer, are disclosed, inter alia in U.S. Pat. Nos. 4,348,376, 4,362,544, 4,331,647, 4,468,457, 4,444,744, 4,460,559, and 4,460,561. In addition, other antibodies are disclosed in U.S. Ser. Nos. 609,607, filed May 14, 1984, now abandoned, and 633,999, filed July 24, 1984, U.S. Pat. No. 4,624,846. The disclosures of the foregoing patents and patent applications are incorporated herein in their entireties by reference. Antigens which are associated with various infectious lesions can also be detected using the method of the invention, and antibodies to such antigens are also disclosed, inter alia, in the aforementioned U.S. Ser. No. 633,999.

As noted above, a-Ids are conventionally produced by challenging an animal with an immunogenically active form of a specific a-Ig. In some cases, this can be achieved merely by injecting the antibody, in a conventional adjuvant, into a suitable animal, e.g., a mouse, sheep, goat, rabbit or the like. Booster shots of antibody are conventionally administered periodically and antiserum is withdrawn after a suitable hyperimmune state is achieved. Antibodies can be recovered from the antiserum by conventional purification procedures, including affinity chromatography on columns to which purified antigen have been bound. Removal of cross-reactive antibodies can be achieved by chromatography over columns to which are bound other cross-reactive antigens.

Alternatively, the conventional techniques for producing monoclonal antibodies can be used. This involves challenging a suitable animal, e.g., a mouse, with an immunogenically active form of the specific antibody, removing lymphocytes, e.g., splenocytes, after a suitable hyperimmune response has been achieved, and fusing the splenocytes with a suitable myeloma cell line. Hybridoma clones are produced conventionally, and screened for specific anti-idiotype activity.

Human hybridomas can be produced by a variety of known techniques, including that disclosed in U.S. Pat. No. 4,464,465 and those described in Kosbor et al., "The production of monoclonal antibodies from human lymphocytes," Immunol. Today 4:72–79, 1983; Kozbor et al., "Human hybridomas constructed with antigen-specific Epstein-Barr virus-transformed cell lines," Proc. Natl. Acad. Sci. 79:6651–6655, 1982; Kozbor et al., "In vitro stimulated lymphocytes as a source of human hybridomas," Eur. J. Immunol. 1984, (in press); Olsson et al., "Human hybridomas producing monoclonal antibodies of predefined antigenic specificity," Proc. Natl. Acad. Sci. (USA) 77:5429–5434, 1980; and Croce et al., "Production of human hybridomas secreting antibody to measles virus," Nature 288:488–489, 1980.

These references disclose methods for producing human monoclonal antibodies. To adapt them to the production of human hybridomas secreting a-Ids, a first step is to remove peripheral blood from patients with, e.g., a specific tumor and/or infections lesion, to which the patient's immune system has generated antibodies, which should also be accompanied by a-Ids to the idiotype a-Ags. Lymphocytes are then separated, e.g., on a Ficoll gradient, and recovered. Alternatively, splenocytes and/or lymphocytes can be removed from the spleen and/or lymph glands or ducts of the patient. The lymphocytes are tested for a-Id productions, e.g., with a-Id and/or by competitive inhibition of Ag/a-Ag complex formation.

Lymphocytes can then be fused with human myeloma cells, e.g., the LICR human myeloma cell line, and a-Id-producing hybridoma cells recovered and cloned. Alternatively, the lymphocytes can be immortalized with Epstein-Barr virus (EBV) and cloned, and clones selected which produce a-Ids. The EBV-immortalized cells can also be fused with human myeloma cells, and a-Id-producing hybridomas can then be isolated and cloned.

Finally, the isolated lymphocytes can be sensitized and stimulated in vitro, e.g., with a-Ag and a mitogen, e.g., poke weed mitogen, in thymocyte conditioned medium or over a feeder layer of macrophages, the cells then being fused and/or immortalized as described hereinabove.

A preferred alternative for producing monoclonal a-Ids has been developed by the present inventor. The method stems from an alternative method of producing monoclonal antibodies, wherein hybridoma cells are injected into a syngeneic animal, most often a mouse, and one or more ascites tumors are grown in appropriate sites in the animal. After several days of growth to establish the tumors, ascites fluid is withdrawn and monoclonal antibodies are readily isolated therefrom.

It has now been found, surprisingly and unexpectedly, that lymphocytes, especially splenocytes, excised from an animal in which an ascites hybridoma tumor has been growing, can be fused with myeloma cells to produce hybridomas which secrete anti-idiotype antibodies to the antibodies secreted by the ascites tumor. Thus, a convenient method is provided whereby both components of the a-Ag/a-Id pair may be produced. The method is applicable to production of a-Id clones which specifically bind antibodies secreted by any hybridoma capable of passage in a host animal. The hybridoma can be passaged as an ascites tumor, a subcutaneous tumor or any other type of viable proliferative hybridoma tumor capable of secreting the a-Ag.

A further improvement in this method may be obtained by *in vitro* stimulation of anti-idiotype clones. This can be effected by, e.g., adding ascites fluid to isolated splenocytes from the animal in which the ascites was grown, in the further presence of a stimulant of B cell production. Suitable such stimulants are known, and include, e.g., pokeweed mitogen. This *in vitro* stimulation is preferably effected in a tissue culture medium. The effect is to selectively concentrate and stimulate the growth of B cells which produce anti-idiotype antibodies. The resultant stimulated cultured cells are then fused with myeloma cells and an increased yield of a-Id hybridomas is observed.

Anti-idiotype monoclonal antibodies offer both technical and commercial advantages over conventional antigen in competitive binding assays. Hybridoma-derived a-IDs can be produced in unlimited quantities with defined specificity and high stability. The hybridoma cell lines producing the a-Id can be frozen in liquid nitrogen and stored indefinitely. The a-Ids offer unique opportunities for biological and chemical modification intended to improve performance characteristics of test kits. For example, a-Id antibody fragments can be used, which can offer advantages over the whole immunoglobulin. Bifunctional hybrids can be used, e.g., those disclosed in U.S. Pat. No. 4,331,647, or similar dual specificity species. Isotype switching can be effected with the a-Ids to effect advantages and/or to permit the use of standardized or universal labels linked to isotype-specific antibodies.

Also, immunoglobulin will often be easier to label and/or bind to solid supports than antigens, since labeling techniques for immunoglobulin are highly developed and are readily standardized.

The ease of production and purification of a-Id monoclonal antibodies from both tissue culture medium or ascites fluid also militates in favor of their use. Furthermore, purified a-Id monoclonal antibodies are cheaper to produce than purified antigen in many cases, especially in the case of tumor markers.

In the event that the specificity of a single a-Id is too narrow to completely block binding of the antigen to the a-Ag, it is possible to select two or more a-Ids from a library having defined inhibitory properties against the a-Ag to achieve suitable inhibition. As noted above, it is also possible to use immunoglobulin fragments for either the a-Ag or a-Id component of the complex and/or for the a-Id used to run the standard curve.

As an illustration of the methods of producing a-Ids and the construction and use of assay kits according to the invention, the following preferred embodiment is set forth in detail. The antibody used as an antigen to stimulate production of a-Id is a purified anti-carcioembryonic antigen monoclonal antibody designated NP-2, whose preparation is described in U.S. patent application Ser. No. 609,607, filed May 14, 1984. The antibody is suspended at a concentration of 1 mg/ml in phosphate buffered saline (PBS, pH 7.2) and frozen at $-20°$ C. until used for immunization for assay.

Immunization Protocol for Hybridoma Production

Two immunization schedules are used to construct NP-2 anti-idiotypes. Six to eight week old Balb/cJ female mice (Jackson Laboratories, Bar Harbor, ME) are injected intraperitoneally (i.p.) with 100 mcg of purified NP-2 in complete Freund's adjuvant (1:1). The animals are given a second i.p. injection of 50 mcg NP-2 in PBS one week later and a final i.p. injection of 50 mcg NP-2 in PBS eight weeks after that. Three days following the final immunization, the animals are sacrificed for fusion.

An alternative immunization protocol involves the isolation of anti-NP-2 activated splenocytes from animals injected with parental hybridoma cell line, P1-A6. In this procedure, female Balb/cJ mice are primed by imp. injections of 0.5 ml pristane (2,6 10,14-tetramethylpentadecane; Aldrich Chemical Co., Milwaukee, WI). The animals are inoculated with $1-2\times10^6$ P1-A6 cells. The mice usually develop ascites tumors after 7–14 days and the ascites fluid is collected via i.p. tap. The animals are sacrificed on day 21 and the splenocytes removed for the fusion step. Preliminary observations have shown that these animals develop an immune response against the idiotype.

Construction of the Hybridoma

The procedure for hybridoma production is a modification of previously described techniques disclosed in Kennett et al., Curr. Topics Microbiol. Immunol., 81 77 (1978); Strike et al., J. Immunol., 132, 1798 (1984). Immunized animals are sacrificed by cervical dislocation and the spleens aseptically removed and teased apart to prepare a single cell suspension of splenocytes in serum-free Dulbecco's Modified Eagles' Medium (DMEM; Gibco Laboratories, Grand Island, NY). The cells are collected by centrifugation and washed one time in DMEM. The total cell numbers are determined by hemocytometer counts using the trypan blue exclusion technique.

Approximately $10^8$ splenocytes are mixed with $2.5\times10^7$ P3X63 - AG8.653 murine myeloma cells (653; ATCC). The supernatant is removed and the pellet is resuspended by gentle tapping. One ml of polyethylene glycol (PEG 4000; Gibco Laboratories) is added to the tube and the cells incubated for 90 seconds at room temperature. Five ml of DMEM is added over a 60 second period followed by an additional 5 ml of DMEM supplemented with 20% fetal bovine serum (D-20) for 60 seconds. The fused cells are then centrifuged for 10 minutes at 500 x g. The final cell pellet is resuspended in 50 ml of 1:1 D20 +D-20 containing HAT (D-HAT) (HAT:hypoxantheneaminopterinthymidine) and added to six 96-well microtiter plates at an approximate concentration of $2.3\times10^5$ cells per well. Cells are fed with D-HAT on days 1, 3, 7, 10 and D-20 weekly threafter until the colonies appear and are assayed (about 2–3 weeks).

Hybridoma Screening Methods and Cloning Procedures.

The initial screen for the presence of NP-2 a-Ids is done using an RIA with NP-2 monoclonal antibody(MAB) as the coating antigen. Polyvinyl chloride microtiter plates are coated with 1 mcg/well of goat anti-mouse Fc (Pel Freeze, Rogers, AR) suspended in 0.05 M carbonate buffer (pH 9.6). One to two micrograms of NP2 are added per well for 1 hour followed by the addition of 50 μl of hybridoma supernatant. $^{125}$I-labeled CEA is then added and each well counted in a Packard Auto Gamma Scintillation Spectrometer (Model 5230). Positive colonies are identified by the inhibition of CEA binding to NP-2.

After freezing aliquots of these positive colonies at −135° C., a number of hybridomas are cloned by the limiting dilution method. Serial dilutions of positive colonies are prepared to a final concentration of 10 cells per ml. A one hundred microliter aliquot is added to each well of a 96 well microliter plate containing a feeder layer of syngeneic splenocytes. In approximately 10-21 days, macroscopic colonies are observed. Only those wells containing one clone (observed microscopically) are reassayed by the previously described RIA.

Positive clones are removed and expanded in tissue culture. Clones are frozen for future use and a manageable number (5-10) subcloned by limiting dilution at a concentration of 0.5-1 cell/well. Subclones are assayed for anti-NP-2 binding activity and positive ones expanded in tissue culture. At this point positive subclones are tested for their effect on CEA binding to NP-2 using a competitive radioimmunoassay (RIA).

Radioimmunoassay to Determine a-Id Blocking Activity.

It is necessary to determine the effect of the concentration of a-Id monoclonal antibody on the binding of CEA to NP-2. This is done using a competitive RIA. A series of test tubes are set up and two ml of 0.01 ml ammonium acetate and 20 ml of NP-2 (1:100) are added to each. Varying concentrations of a-Id plus 50ul of I-125 labeled CEA (approximately $10^6$ cpm/ml) are added and the tubes incubated for 30 minutes at 45° C. After the incubation period, two ml of Z-gel (zirconylphosphate) are added and the tubes spun immediately at 1000 x g for 5 minutes. The gel is washed one time with ammonium acetate and the tubes counted in a gamma counter.

The appropriate positive and negative controls are run to insure the accuracy of the results (including irrelevant MAB). Only those a-Id subclones which effectively inhibit the binding of CEA to NP-2 MAB are maintained. It is expected that a number of subclones will show blocking activity. These cells are expanded in tissue culture and frozen at −135° C. Large-scale production of desired MAB will involve the preparation of ascites fluid from Balb/cJ mice.

Preparation of the Ascites Fluids Containing Monoclonal Antibodies.

Hybridoma cells are grown in DMEM supplemented with 10% fetal calf serum. The cells are sedimented at 500 x g for 10 minutes at 4° C., and are resuspended in serum-free medium. Cell density is determined by counting the suspended cells in a hemocytometer, and viability by trypan blue exclusion.

Balb/cJ mice, 8–10 weeks old, are primed by intraperitoneal injections of one ml pristane 3 to 4 days prior to the inoculation. The inoculation is accomplished by intraperitoneal injections of $1-2 \times 10^6$ viable cells. To obtain the ascites fluids, mice are anesthetized with metophane (Pitman-Moore, Inc., Washington Crossing, NJ) and the fluids are tapped by means of a 20 ga. hypodermic needle into sterile capped plastic culture tubes. To remove the cells, the ascites fluids are centrifuged at 500 x g for 15 minutes at 4° C. and the supernatant containing the ascites fluids is transferred into a sterile containing the ascites fluids transferred into a sterile container and kept frozen at −20° C. to −30° C. until needed.

Isotyping of a-Id MAB.

The mouse antibody isotype of anti-NP-2 a-Id is determined using affinity purified, heavy chain specific anti-mouse Ig (Cappel Laboratories, Malvern, PA) in a modified ELISA with the a-Ids as the coating antigens. Anti-idiotypic IgG monoclonal antibodies are purified as described hereinafter.

Purification of the Monoclonal Antibodies From Ascites Fluids.

The purification of the monoclonal antibodies involves 3 major steps: (1) Ammonium sulfate fractionation of the crude ascites fluids to obtain the crude gamma-globulin fraction; (2) Ion-exchange chromatography (IEC) on DEAE-cellulose; and (3) Final purification of the IgG fraction by chromatography on hydroxylapatite column, which is developed with linear gradient of potassium phosphate.

Ammonium sulfate fractionation.

The ascites fluids are thawed, pooled if necessary, and centrifuged at 1800 x g for 15 min. at ambient temperature; the supernatant is then filtered through glass wool. An aliquot of saturated solution of $(NH_4)_2SO_4$ is adjusted to pH 7.5 with concentrated ammonium hydroxide (30%). Using a burette, a volume of saturated solution of $(NH_4)_2SO_4$ is added dropwise to the stirring ascites fluids to affect a final concentration of 40% of saturation. Upon completion the suspension is left to stir at room temperature for 120 min. The suspension is transferred into capped centrifuge tubes and the precipitate is harvested by centrifugation at 1800 x g for 15 min. at room temperature. The supernatant is discarded and the pellet is dissolved into a small volume of PBS. The dissolved pellet is dialyzed at 4° C. against 5 to 6 changes of 1000 volumes each of 0.01 M sodium phosphate pH 8.0. (Three changes per day with approximately 3 to 4 hours between changes). Part of the turbidity formed during the dialysis is removed by centrifugation at 1800 x g for 15 min. at room temperature.

Ion-exchange Chromatography on Column of DEAE-Cellulose.

Seventy-five grams of DE-52 (Whatman, Clifton, NJ) are equilibrated with 0.5M sodium phosphate, pH 8.0, at room temperature with occasional mixing. This amount of ion-exchange cellulose (IEC) is sufficient to process material obtained from 100 to 120 ml ascites fluids. After 2 to 3 hours, the IEC is washed with 0.01M sodium phosphate pH 8.0 until the pH and the conductivity of the effluent and the affluent are identical. The IEC is washed with at least one bed volume of 0.01M sodium phosphate pH 8.0.

The Ig sample is loaded onto the column and chromatographed until the absorbance at 280 nm of the effluent returns to baseline, the buffer is changed to 0.025M sodium phosphate pH 8.0 and the elution continues at the same flow rate. The protein fraction which elutes at this concentration of phosphate contains the mouse IgG, and it is composed of IgG and a small quantity of another protein that exhibits migration in immunoelectrophoresis (perhaps transferrin). This contaminant is removed readily by chromatography on hydroxylapatite. The IgG fraction is concentrated, if necessary, by ultrafiltration using Amicon YM-30 membranes, and then dialyzed at 4° C. against 4 changes of 0.01M potassium phosphate pH 6.8 containing 0.02% sodium azide, 2000 ml each. A sample is taken for analysis by immunoelectrophoresis and PAGE.

Chromatography on Hydroxylapatite.

One gram of hydroxylapatite (HA; BIORAD, Richmond,CA) per 20 mg of IEC-purified IgG is dispersed in 6 volumes (ml/g) of 0.01M potassium phosphate(pH 6.8). The HA bed is packed over approximately 0.5 cm of Sephadex G-25 fine (Pharmacia, Piscataway, NJ) in a wide and short column (2.5×20cm). Both the Sephadex layer and HA are packed at a flow rate of 12 $ml \times hr^{-1} \times cm^{-2}$. The IgG fraction is centrifuged at 1800 x g to remove particulate matter (15 min. R.T.) and then applied to the column at a reduced flow rate of 6 $ml \times hr^{-1} \times cm^{-2}$. The column is eluted with at least one bed volume of buffer or until the absorption of the effluent (at 280 nm) is baseline.

The column is connected to a gradient former and eluted with a linear gradient of potassium phosphate pH 6.8 from 0.01M to 0.03M (total volume of the gradient is equal to 10 bed volumes).

The absorbance of the effluent is followed at 280 nm, and the IgG fraction collected into a sterile and pyrogen-free container. The IgG preparation is concentrated to 10 mg/ml by ultrafiltration, using Amicon YM-30 membrane and stored aseptically at 4° C.

The monoclonal antibody preparation is tested for purity and immunoreactivity by: (a) Immunoelectrophoresis against anti-whole serum and anti-mouse IgG; (b) Polyacrylamide gel electrophoresis in nondenaturing gels; and/or (c) The IgG preparation is labeled with $^{125}I$ to specific activity of 12–15 uCi per mcg, and analyzed for immunoreactivity and purity using the following affinity matrices: CEA coupled to Sepharose and anti-mouse IgG coupled to Sepharose. The former is used to test the immunoreactivity and the latter the percentage of IgG in the preparation.

Construction of an RIA Diagnostic Kit Using a-Id MAB as Antigen.

In general, this kit is a competitive immunoassay in which a standard concentration of radiolabelled anti-idiotype monoclonal antibody and patients' sera is added to anti-CEA coated polyvinyl chloride test tubes (a-CEA-PVC). The concentration of CEA in the sera is derived from a standard curve by correlating the inhibition of anti-idiotype binding to a-CEA-PVC by the patients' sera.

1. Preparation of a-CEA-PVC.

Polyvinyl chloride test tubes are coated with anti-CEA monoclonal antibodies (NP-2) suspended in a carbonate buffer at pH 9.6. Unreactive sites on the tubes (which can result in non-specific binding) are blocked with 3% bovine serum albumin in the same buffer. These tubes can be stored at 4° C. for 6–12 months (Kennet, R. H., *Monoclonal Antibodies;* R. H. Kennet, T. J. McKearn, K. B. Bechtol, eds., Plenum Press, N.Y., p. 376, 1981).

2. Determining the Relationship of Anti-Idiotype Binding to anti-CEA Monoclonal Antibodies and CEA concentration It is necessary to determine the concentration of a-Id monoclonal antibody that will completely inhibit the binding of CEA to anti-CEA monoclonal antibody. This is done to define the relationship between anti-idiotype binding to anti-CEA monoclonal antibody and CEA protein concentration. In order to accomplish this aspect of test kit development, varying concentrations of $^{125}I$-labelled a-Id monoclonal antibody are added with known concentrations of CEA to a-CEA-PVC. Inhibition curves are generated which relate the blocking activity of a-Id with CEA protein concentration. The a-Id is then used to generate standard curves in the diagnostic test kit.

3. Use of Anti-Idiotype Monoclonal Antibody in a Diagnostic Test Kit.

This test kit takes advantage of the ability of a-Id MAB to act as a "surrogate antigen" for determination of CEA concentration in human sera. The following components are to be supplied with the kit:

a-CEA-PVC, prepared as described above;
$^{125}I$-labelled anti-idiotype monoclonal antibody (one standard concentration) conventionally labeled, e.g., by the Chloramine-T method;
non-labeled a-Id MAB (for generating standard inhibition curves);
phosphate buffered saline (PBS) buffer tablets. The test scheme is organized as follows:

1. Generate a standard inhibition curve using known concentrations of a-Id MAB. The curve is generated over a range of a-Id concentrations corresponding to CEA concentrations of 1–100mg/ml. In this step, a-Id MAB is added to a-CEA-PVC in 3 ml of PBS.
2. Add the patient's serum to a-CEA-PVC. It is usually unnecessary to extract protein from sera as required in many commercially available kits, because of the high specificity of monoclonal antibodies.
3. Incubate the tubes at 45° C. for 20 minutes.
4. Wash the tubes three times with PBS. This involves the addition of 3 ml PBS to each tube and the subsequent pouring of the liquid into a waste bottle. The tubes are then blotted dry.
5. Add $^{125}I$-labeled a-Id monoclonal antibody to each tube and incubate for 30 minutes at 45° C.
6. Wash the tubes three times with PBS and blot dry.
7. Count the tubes in a gamma scintillation spectrometer.
8. Determine the CEA concentration in the patient's serum from the standard inhibition curve, i.e., the amount of CEA in the serum is related to the inhibitory effect on a-Id binding to a-CEA-PVC.

There are a number of advantages of the above kit over those presently on the market. The present kit has higher sensitivity, since the standard inhibition curve can be generated over a greater range of CEA concentration by manipulating the amount of a-Id monoclonal antibody. The present kit also has greater accuracy. The assay does not vary from lot to lot, since specific a-Id monoclonal antibody is available in unlimited supply from cloned hybridoma cultures. In addition, there is no need for continued biochemical isolation of CEA, thereby cutting costs and eliminating lot to lot variability.

A non-isotopic diagnostic kit using a-Id MAB as antigen can easily be constructed. This kit is similar to that described hereinabove, except for the use of a peroxidase-conjugated a-Id monoclonal antibody as surrogate antigen instead of one radiolabeled with $^{125}I$. The procedure is the same as that described for the RIA, with an additional step involving the addition of a chromogen (such as orthophenylenediamine) in the presence of $H_2O_2$ and the determination of CEA binding using a spectrophotometer. The peroxidase-conjugated a-Id can be conventionally prepared, e.g., by the procedure of conjugation with glutaraldehyde.

It will be appreciated that the foregoing illustration can be modified further to substitute for the anti-CEA specific antibody and antibody, preferably a monoclonal antibody, which specifically binds another tumor-associated antigen, e.g., alpha-fetoprotein (AFP), human chorionic gonadotropin (HCG), colon-specific antigen-p (CSAp), prostatic acid phosphatase (PAP) and the like. Alternatively, the specific antibody can be an antibody which specifically binds a marker associated with an infectious lesion, e.g., an antibody against a virus, a bacterium or other infectious microorganism, a hormone, an enzyme and the like. The method of the invention can be utilized in any assay wherein the antigen is detected by virtue of its inhibition of the reaction between an antibody and its complementary anti-idiotype antibody. More generally, any competitive immunoassay which detects antigen by virtue of its ability to inhibit the formation of an antigen/antibody complex can be modified to substitute anti-idiotype antibody for the antigen, typically in a form wherein either the a-Id or a-Ag is bound to a solid support, and the other component of the pair is labeled.

The foregoing general disclosure and examples are meant to be illustrative only and one of ordinary skill in the art will appreciate that further variations and modifications may be made without departing from the spirit or the scope of the invention, which is defined by the appended claims.

What is claimed is:

1. A method of producing a monoclonal anti-idiotype antibody, comprising the steps of:
    (a) fusing lymphocytes from an animal in which a tumor capable of secreting idiotype antibodies has been grown, with myeloma cells; and
    (b) isolating and cloning resultant hybridoma cells secreting monoclonal antibodies which specifically bind an epitope on the hypervariable region of said idiotype antibodies.

2. The method of claim 1, wherein said animal is a mouse.

3. The method of claim 1, wherein said myeloma cells are murine myeloma cells.

4. The method of claim 1, wherein said lymphocytes are splenocytes.

5. The method of claim 4, wherein in step (a) said splenocytes are grown *in vitro* in a tissue culture medium, ascites fluid from the animal in which the ascites tumor was grown is added to the splenocytes, in the further presence of a stimulant of B cell production, and resultant stimulated cultured splenocytes are then fused with said myeloma cells.

6. The method of claim 5, wherein said stimulant of B cell production is pokeweed mitogen.

* * * * *